US009220689B2

(12) United States Patent
Armes et al.

(10) Patent No.: US 9,220,689 B2
(45) Date of Patent: *Dec. 29, 2015

(54) NANOPARTICLES

(71) Applicant: DSM IP ASSETS B.V., Heerlen (NL)

(72) Inventors: Steven Armes, Sheffield (GB); Jian-Jun Yuan, Osakidai (JP)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,283

(22) Filed: Oct. 11, 2013

(65) Prior Publication Data

US 2014/0037741 A1    Feb. 6, 2014

Related U.S. Application Data

(60) Continuation of application No. 13/363,114, filed on Jan. 31, 2012, now Pat. No. 8,580,311, which is a division of application No. 12/438,591, filed as application No. PCT/EP2007/007729 on Sep. 5, 2007, now abandoned.

(30) Foreign Application Priority Data

Sep. 6, 2006 (GB) .................................... 0617480.9

(51) Int. Cl.
| | |
|---|---|
| *A61K 9/51* | (2006.01) |
| *B82Y 30/00* | (2011.01) |
| *A61K 9/50* | (2006.01) |
| *C08K 3/36* | (2006.01) |
| *C08K 9/00* | (2006.01) |
| *C09D 7/12* | (2006.01) |
| *G02B 1/111* | (2015.01) |
| *C08K 9/02* | (2006.01) |
| *C08L 53/00* | (2006.01) |

(52) U.S. Cl.
CPC ............... *A61K 9/5089* (2013.01); *A61K 9/501* (2013.01); *C08K 3/36* (2013.01); *C08K 9/00* (2013.01); *C09D 7/1291* (2013.01); *G02B 1/111* (2013.01); *C08K 9/02* (2013.01); *C08K 2201/013* (2013.01); *C08L 53/00* (2013.01); *Y10T 428/254* (2015.01); *Y10T 428/2998* (2015.01)

(58) Field of Classification Search
None
See application file for complete search history.

(56) References Cited

U.S. PATENT DOCUMENTS

| | | | | |
|---|---|---|---|---|
| 4,540,498 | A * | 9/1985 | Wu et al. ........................ | 507/221 |
| 4,965,091 | A | 10/1990 | Fratello et al. | |
| 5,100,471 | A | 3/1992 | Winnik et al. | |
| 6,685,966 | B1 * | 2/2004 | Dominique et al. .......... | 424/490 |
| 7,138,161 | B2 | 11/2006 | Noguchi | |
| 2002/0068805 | A1 | 6/2002 | Futami et al. | |
| 2003/0112491 | A1 | 6/2003 | Albert et al. | |
| 2004/0135126 | A1 | 7/2004 | Schwark et al. | |
| 2005/0220880 | A1 * | 10/2005 | Lewis et al. .................. | 424/486 |
| 2006/0078754 | A1 | 4/2006 | Murakami et al. | |
| 2006/0172128 | A1 | 8/2006 | Shinohara | |
| 2006/0181774 | A1 | 8/2006 | Ojima et al. | |

FOREIGN PATENT DOCUMENTS

| | | |
|---|---|---|
| JP | 2001-247820 | 9/2001 |
| JP | 2002-317152 | 10/2002 |
| JP | 2004-300172 | 10/2004 |
| JP | 2006-126737 | 5/2006 |
| JP | 2006-178041 | 7/2006 |
| WO | 03/074026 | 9/2003 |
| WO | WO 03074026 A1 * | 9/2003 |
| WO | 2004/085493 | 10/2004 |
| WO | 2004/096422 | 11/2004 |
| WO | WO 2004096422 A1 * | 11/2004 |

OTHER PUBLICATIONS

Liu, S.; Weaver, J. V. M.; Tang, Y.; Billingham, N. C; Armes, S. P., Synthesis of Shell Cross-Linked Micelles with pH-Responsive Cores Using ABC Triblock Copolymers, Macromolecules, 2002, 35, 6121-6131.*
Beck, J.S., et al. (A New Family of Mesoporous Molecular Sieves Prepared with Liquid Crystal Templates, J. Am. Chem. Soc. 1992, 114, 10834-43).*
International Search Report for PCT/EP2007/007729, mailed Apr. 21, 2008.
Depasse (Interaction between silica and hydrophobic cations, 35 Brit. J. Indus. Med. 32, 32 (1978)).
Huo (A New Class of Silica Cross-Linked Micellar Core-Shell Nanoparticles, 128 J. Am. Chem. Soc. 6447, S1-S13 (2006)).
Huo (A New Class of Silica Cross-Linked Micellar Core-Shell Nanoparticles, 128 J. Am. Chem. Soc. 6447-53 (2006)).
Caruso, Preparation and Characterization of Ordered Nanoparticle and Polymer Composite Multilayers on Colloids, Langmuir, vol. 15, 1999, pp. 8276-8281 (XP002376288).
Database WPI Week 200553, Derwent Publications Ltd., London, GB; AN 2005-521967, XP002475930, JP 2005-181543A (Bridgestone Corp) Jul. 7, 2005.
Jang et al, Synthesis and characterization of titania coated polystyrene spheres for electronic ink, Synthetic Metals 152, 9-12 (2005).
Lu et al, Synthesis and Crystallization of Hybrid Spherical Colloids Composed of Polystyrene Cores and Silica Shells, Langmuir 2004, 20, 3464-3470.
U.S. Appl. No. 12/438,596, filed Jun. 30, 2009.
U.S. Appl. No. 12/676,084, filed Mar. 2, 2010.
Imhof, *Preparation and Characterization of Titania-Coated Polystyrene Spheres and Hollow Titania Shells*, Langmuir, 2001, 17, p. 3579-3585.
Caruso, *Magnetic Core-Shell Particles: Preparation of Magnetite Multilayers on Polymer Latex Microspheres*, Adv. Mater., 1999, 11, p. 950-953.

* cited by examiner

*Primary Examiner* — H. Sarah Park
(74) *Attorney, Agent, or Firm* — Nixon & Vanderhye P.C.

(57) ABSTRACT

Methods for the preparation of polymer-templated core-shell nanoparticles include the steps of (a) preparing a cationic polymeric core material comprising polymeric micelles, and (b) coating the core material with a silica-comprising shell by depositing the shell onto the polymeric micelles from at least one silica precursor to form the core-shell nanoparticles. Compositions which include the core-shell nanoparticles are adapted to facilitate controlled delivery of at least one active agent into a system in response to controlled changes in the pH of the system.

13 Claims, 14 Drawing Sheets

NANOPARTICLES

This application is a continuation of commonly owned U.S. application Ser. No. 13/363,114, filed 31 Jan. 2012 (now U.S. Pat. No. 8,580,311) which is a divisional of U.S. application Ser. No. 12/438,591, filed on 28 Aug. 2009 (now abandoned), which is the U.S. national phase of International Application No. PCT/EP2007/007729 filed 5 Sep. 2007, which designated the US and claims priority to Great Britain Application No. 0617480.9, filed 6 Sep. 2006, the entire contents of each of which are hereby incorporated by reference.

The present invention is concerned with novel nanoparticles. More specifically, the invention relates to core-shell silica-copolymer nanoparticles, methods for their preparation, and their potential uses.

There is growing academic and industrial interest in the synthesis and applications of nanoparticles, most particularly nanoparticles having a core-shell structure in view of their potential use as delivery vehicles for active materials such as drugs. Consequently, much prior art is devoted to the preparation of nano-sized particles of this type.

Specifically, several authors have considered the potential applications of core-shell nanoparticles comprising silica and, in this context, attention has been devoted to the synthesis of block copolymer-templated silica structures, and studies of their properties and possible uses. Moreover, the presence of core-forming materials which allowed for the possibility of achieving triggered release of active materials from the core of the particles could offer significant opportunities.

It is known that biomineralisation of silica, or biosilicification, occurs in water under ambient conditions for various biological systems, such as diatoms and sponges. Moreover, this natural process leads to hierarchical structures and multiple morphologies with precise nanoscale control, features which continue to elude materials scientists. Ideally, any biomimetic approach to silica synthesis would be both environmentally benign and controllable, in order to allow for the generation of a range of structures and morphologies.

Recent improvements in the understanding of biosilicification have resulted in some studies which have successfully demonstrated silica formation under ambient conditions.

Furthermore, it is well known that block copolymers can self-assemble into a wide range of nanostructures that can be used for controlling the formation of various inorganic materials. However, block copolymer-mediated silica formation is seldom reported. Moreover, the production of such particles in a chemically efficient manner that allow for morphological and structural control remains a major challenge.

Silica-based core-shell nanoparticles have been suggested for various bioanalytical applications, such as drug delivery, bioimaging and biolabeling. In such cases, the particles have been previously synthesised by coating functional cores with silica shells either by using Stöber chemistry or by means of a microemulsion approach. Both methods do, however, require the use of non-ideal conditions, such as elevated temperatures, non-physiological pH values, and the presence of large amounts of surfactants and/or organic co-solvents.

It is apparent, therefore, that there is scope for the development of alternative nano-sized particles, which may be obtained using convenient reaction conditions.

According to a first aspect of the present invention, there is provided a composition comprising core-shell nanoparticles, wherein said nanoparticles comprise:
(a) cationic core material comprising polymer; and
(b) shell material comprising silica.

Preferably, the core material comprises copolymer micelles, more preferably diblock copolymer micelles. Most preferably, said diblock copolymer micelle has a core comprising at least one block of a first polymer and a corona comprising at least one block of a second polymer, wherein said second polymer is different to said first polymer.

Preferably, said copolymer comprises a first polymer and a second polymer which both comprise amino-based (alk)acrylate monomer units, more preferably tertiary amino-based (alk)acrylate units, most preferably tertiary aminoalkyl (alk) acrylate units. Particularly preferably, said (alk)acrylate units comprise acrylate or, more particularly, methacrylate units.

In preferred embodiments, said tertiary aminoalkyl methacrylate units comprise dialkylaminoalkyl methacrylate units, especially dialkylaminoethyl methacrylate units. In a particularly preferred embodiment, said copolymer comprises poly[2-(diisopropylamino)ethyl methacrylate)-block-2-(dimethylamino)ethyl methacrylate] (PDPA-PDMA).

According to the invention, said micelles may either be non-crosslinked or shell crosslinked (SCL) micelles based on said polymers. Thus, especially preferred embodiments envisage non-crosslinked or shell crosslinked micelles based on tertiary amine methacrylate-derived block copolymers such as poly[2-(diisopropylamino)ethyl methacrylate)-block-2-(dimethylamino)ethyl methacrylate].

The conventional synthetic route to shell crosslinked micelles involves covalent stabilization of the micelle coronal chains, although polyion crosslinking has also been recently suggested. However, there are no literature reports of micelle shell cross-linking via biomineralization.

In the present invention, crosslinking of the micelles of said tertiary amino-based (alk)acrylate copolymers is most conveniently achieved by partially or fully quaternising the tertiary amino groups of said copolymers with bifunctional quaternising agents. Thus, in the case of the most preferred embodiment of the first aspect of the invention, partial crosslinking of poly[2-(diisopropylamino)ethyl methacrylate)-block-2-(dimethylamino)ethyl methacrylate] (PDPA-PDMA) may be achieved by selective quaternisation/crosslinking of the PDMA chains with a suitable bifunctional quaternising agent, for example a bis(haloalkoxy)alkane, such as 1,2-bis-(iodoethoxy)ethane (BIEE). In this most preferred embodiment, the PDPA chains remain essentially unquaternised.

The invention also envisages analogous non-crosslinked quaternised derivatives, wherein quaternisation is achieved by means of monofunctional quaternising agents, such as alkyl halides, in particular alkyl iodides such as iodomethane. However, it is believed that control of the silica deposition process may be enhanced in the case of crosslinked materials.

The degree of polymerisation of the polymer is preferably controlled within specified limits. Thus, in the most preferred embodiment of the invention, the degree of polymerisation of the PDPA-PDMA copolymer is preferably controlled such that the mean degree of polymerisation of the PDPA falls in the range of 20-25 and the mean degree of polymerisation of the PDMA falls in the range of 65-70, with particularly favourable results having been obtained with the PDPA$_{23}$-PDMA$_{68}$ copolymer, wherein the subscripts denote the mean degrees of polymerisation of each block. In the said embodiment, PDPA units form the cores of the micelles and PDMA units form the coronas of the micelles.

Preferably, said shell material comprises silica which is deposed on said core material from at least one silica precursor. Optionally, said at least one silica precursor may comprise an inorganic silicate, for example an alkali metal silicate, such as sodium silicate. However, preferred silica precursors comprise organosilicate compounds, especially alkyl silicates such as tetramethyl orthosilicate or tetraethyl orthosilicate. Most preferably, said silica precursor comprises tetramethyl orthosilicate. Said treatment is found to effectively crosslink the copolymer chains in uncrosslinked micelles, and thereby stabilise the micelles towards dissociation.

Preferably, said nanoparticles have a particle size in the region of from 10-100 nm, more preferably from 20-50 nm, most preferably from 30-40 nm and, particularly preferably, the particle size is around 30 nm.

Preferably the nanoparticles have an average specific size g (where g=½×(length+width)) of about 300 nm or less. More preferably the particles have an average size of about 200 nm or less. Even more preferably the particles have an average size of about 100 nm or less. Preferably the particles have an average size of 1 nm or more. More preferably the particles have an average size of about 10 nm or more.

Preferably the average specific size of the void is 1 nm or more, more preferably 3 nm or more, even more preferably 6 nm or more. Preferably the average specific size of the void is 100 nm or less, more preferably 80 nm or less, even more preferably 70 nm or less.

Preferably the shell is at least 1 nm thick, more preferably at least 5 nm, even more preferably at least 10 nm. Preferably the shell is 75 nm thick or less, more preferably 50 nm or less, even more preferably 25 nm or less.

In a particular embodiment of the first aspect of the invention there is provided a composition comprising core-shell nanoparticles, wherein said nanoparticles comprise:
  (a) cationic core material comprising a copolymer micelle; and
  (b) shell material comprising silica
wherein said nanoparticles have an anisotropic rod-like morphology. Preferably, in said embodiment of the invention, said copolymer micelle comprises a diblock or triblock copolymer.

According to a second aspect of the present invention, there is provided a method for the preparation of a composition comprising core-shell nanoparticles according to the first aspect of the invention, said method comprising the steps of:
  (a) preparing a cationic core material comprising polymer; and
  (b) coating said core material with a shell comprising silica.

The polymeric core material may be prepared by any suitable polymerisation technique, but particularly favourable results are achieved when employing methods such as group transfer polymerisation and controlled radical polymerisation. Said core material is then coated with silica by treatment with a suitable silica precursor.

The method according to the second aspect of the invention is particularly suited to the preparation of the compositions comprising core-shell nanoparticles according to the more preferred and most preferred embodiments of the first aspect of the invention. Thus, particularly preferred embodiments envisage the preparation of cationic diblock copolymers by sequential monomer addition using group transfer polymerisation of tertiary aminoalkyl methacrylates.

Full or partial quaternisation of said copolymers may be achieved by any of the standard quaternisation techniques reported in the literature. Typically, therefore, treatment of said tertiary amino-based copolymers with alkyl halides, most particularly alkyl iodides such as iodomethane, in suitable inert solvents facilitates the preparation of non-crosslinked quaternised derivatives, whilst crosslinked quaternised copolymers are obtained by treatment of the tertiary amino copolymers with bifunctional quaternising agents such as bis(haloalkoxy)alkanes, for example 1,2-bis-(iodoethoxy)ethane, in appropriate inert solvents. Typically, said quaternisation reactions are carried out by treating the tertiary amino copolymers with quaternising agents at or around ambient temperature (20-30° C.), preferably about 25° C., for a period of time of between 1-100 hours, preferably between 24 and 72 hours.

Deposition of silica is carried out by simply treating the cationic polymers with suitable silica precursors under mild conditions. Thus, in the case of the preferred copolymer micelles, these materials may be stirred with a silica precursor, typically an organosilicate compound, especially an alkyl silicate such as tetraethyl orthosilicate or, most preferably, tetramethyl orthosilicate, for between 10 and 60 minutes at 5-30° C. and a pH of between 6.2 and 9.0. In a typical reaction, PDPA-PDMA copolymer micelles may be treated with tetramethyl orthosilicate for 20 minutes at 20° C. and pH 7.2. The method of the second aspect of the present invention does, in this regard, offer significant advantages over the methods of the prior art, which require that silica deposition procedures should be carried out at low pH values, and typically at pH 1.

According to a third aspect of the present invention, there is provided a composition adapted to facilitate controlled delivery of at least one active agent into a system, said composition comprising core-shell nanoparticles according to the first aspect of the invention, wherein said composition is adapted to provide said controlled delivery in response to controlled changes in the pH of said system.

According to a fourth aspect of the present invention, there is provided a method for facilitating controlled delivery of at least one active agent into a system, said method comprising introducing a composition according to the third aspect of the invention into said system and changing the pH of the system in a controlled manner so as to facilitate said delivery.

Preferred examples of said active agent include, for example, drugs, dyes and catalysts, and suitable systems into which they might be delivered include such diverse examples as human and animal bodies, coatings and chemical reactors. In the case of the most preferred compositions according to the first aspect of the invention, wherein said compositions comprise copolymers which comprise tertiary amine-based alkyl (meth)acrylate units, controlled delivery of active agents may be achieved by introducing said composition into a system and adjusting the pH of a system to a value of less than 6 by addition of a suitable acidic agent.

According to a further aspect of the present invention, there is provided a thin-film coating comprising the present nanoparticles. As used herein, "thin-film" refers to coatings having an average thickness of 500 nm or less.

According to a further aspect of the present invention, there is provided an optical coating comprising the present nanoparticles. As used herein, the term "optical coatings" refers to coatings with an optical function as major functionality. Examples of optical coatings include those designed for anti-reflective, anti-glare, anti-dazzle, anti-static, EM-control (e.g. UV-control, solar-control, IR-control, RF-control etc.) functionalities. Preferably the present coatings have an anti-reflective functionality. More preferably the present coatings are such that, when measured for one coated side at a wavelength between 425 and 675 nm (the visible light region), the minimum reflection is about 2% or less, preferably about 1.5% or less, more preferably about 1% or less.

It will be apparent that it may be necessary to remove some or all of the core material from the particle in order to achieve some of the benefits of the present particles. This may be achieved in any suitable manner at any suitable point in the production process. Preferred methods include, for example, thermodegradation, photodegradation, solvent washing, electron-beam, laser, catalytic decomposition, and combinations thereof. Therefore, the scope of the present invention encompasses core-shell nanoparticles where the core is present and where the core has been at least partially removed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention will be described in further detail with particular reference to the accompanying drawings, in which:

FIG. 1 schematically shows the formation of core-shell silica nanoparticles obtained by biomineralization of tetramethyl orthosilicate (TMOS) using either shell crosslinked (SCL) or non-crosslinked cationic block copolymer micelles as templates. Both routes lead to well-defined, core-shell copolymer-silica nanoparticles. The use of non-crosslinked micelles, as shown in the upper route, additionally leads to in situ silica crosslinking.

FIG. 2 presents TEM images of copolymer-silica nanoparticles: (A) synthesised by directly using non-quaternised $PDPA_{23}$-$PDMA_{68}$ copolymer micelles as templates; and (B) formed using partially quaternised copolymer micelles (50% with respect to the PDMA shell); the inset in (B) is a typical high magnification image obtained after dispersing the same particles directly into an acidic solution (pH 2). The scale bars are 100 nm.

FIG. 3 displays TEM images obtained for: (A) core-shell copolymer-silica nanoparticles prepared by stirring a mixture containing 2.0 ml of a 0.25 w/v % aqueous solution of partially quaternised shell crosslinked micelles [30% target degree of crosslinking for the PDMA chains] solution and 2.0 ml TMOS for 40 minutes (the top inset shows a representative hollow silica nanoparticle after pyrolysis of the copolymer component by calcination at 800° C.; the lower inset highlights a typical core-shell particle); (B) core-shell copolymer-silica nanoparticles formed using partially quaternised SCL micelles (50% target degree of crosslinking with respect to the PDMA chains) using the same biomineralisation conditions as those employed in (A); (C) core-shell copolymer-silica nanoparticles formed 40 minutes after stirring an initially homogeneous solution comprising 2.0 ml of a 0.25 w/v % aqueous solution of partially quaternised SCL micelles [30% target degree of crosslinking for the PDMA chains], 2.0 ml TMOS and 2.0 ml methanol; and (D) core-shell copolymer-silica nanoparticles formed 120 minutes after stirring using the same conditions as described in (C). The scale bars are 50 nm in each case.

FIG. 4 shows the particle size distribution of the core-shell copolymer-silica nanoparticles prepared from the $PDPA_{23}$-$PDMA_{68}$ copolymer (50% quaternised coronal PDMA chains using iodomethane) estimated from the TEM image shown in FIG. 2B. These particles have a TEM number-average diameter of 28±3 nm and an intensity-average diameter of 34 nm, as judged from DLS measurements.

FIG. 5 shows a transmission electron micrograph of silica nanoparticles obtained from micelle templates prepared using the quaternised $PDPA_{23}$-$PDMA_{68}$ copolymer (100% quaternisation of the PDMA chains), using biomineralization conditions which were the same as those used for templating micelles prepared with the 50% quaternised copolymer; in this case there appears little or no evidence for the formation of core-shell copolymer-silica nanoparticles, and silification appears to occur throughout the micelle interior.

FIG. 6 shows a transmission electron micrograph of silica nanoparticles (the same particles as shown in FIG. 2B, formed by 50% quaternised $PDPA_{23}$-$PDMA_{68}$ micelles) after dispersing in acidic solution at pH 2 with the aid of an ultrasonic bath.

FIG. 7 illustrates $^1$H NMR spectra of: (a) a molecular solution of the $PDMA_{68}$-$PDPA_{23}$ diblock copolymer (50% quaternised PDMA block using iodomethane) in $D_2O$/DCl at pH 2 (signal G at δ 1.3-1.4 is due to the four equivalent methyl groups of the protonated DPA residues); (b) micelles for the same copolymer obtained in $D_2O$ at pH 7 (there is no longer a G signal at δ 1.3-1.4 due to the DPA residues since the PDPA block becomes deprotonated and forms hydrophobic micelle cores at this pH; (c) silica-coated nanoparticles derived from $PDPA_{23}$-$PDMA_{68}$ diblock copolymer micelles (50% quaternised PDMA block) in $D_2O$ at pH 2 (the signal G at δ 1.3-1.4 corresponds to the protonated PDPA chains within the micelle cores); and (d) the same silica-coated nanoparticles in $D_2O$ at pH 7 (signal G at δ 1.3-1.4 disappears, indicating that the PDPA chains in the micelle cores become hydrophobic due to deprotonation).

Figure 10:
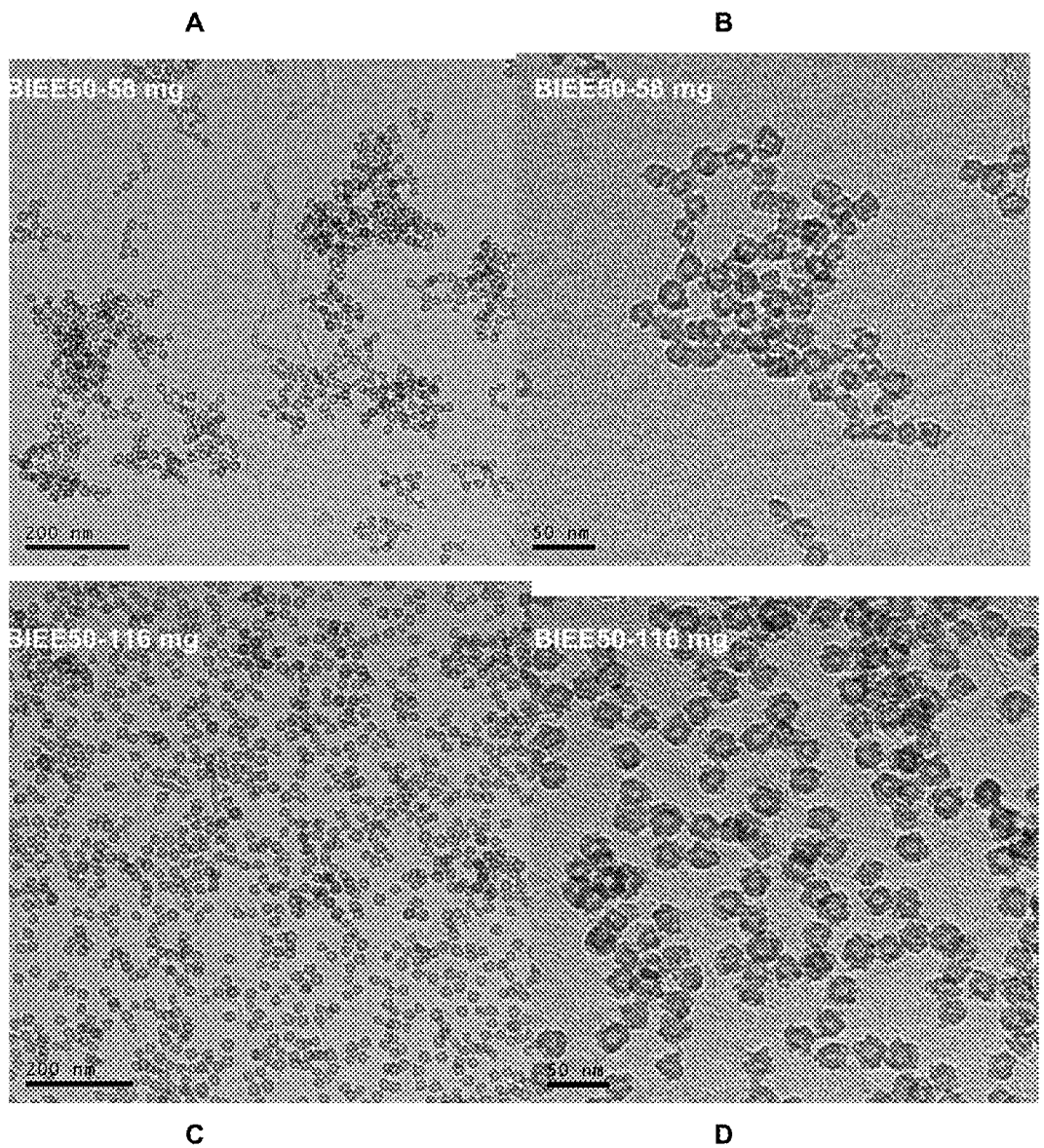

FIG. 10 shows Transmission Electron Micrographs of core-shell copolymer-silica nanoparticles obtained by stirring a mixture containing 2.0 ml of a 0.25 wt. % aqueous solution of partially quaternised copolymer micelles (50% target degree of crosslinking with respect to the PDMA shell, using BIEE for quaternisation) and either (images A, B) 58 mg or (images C, D) 116 mg of TMOS at 20° C. for 20 minutes at pH 7.2.

Figure 11:
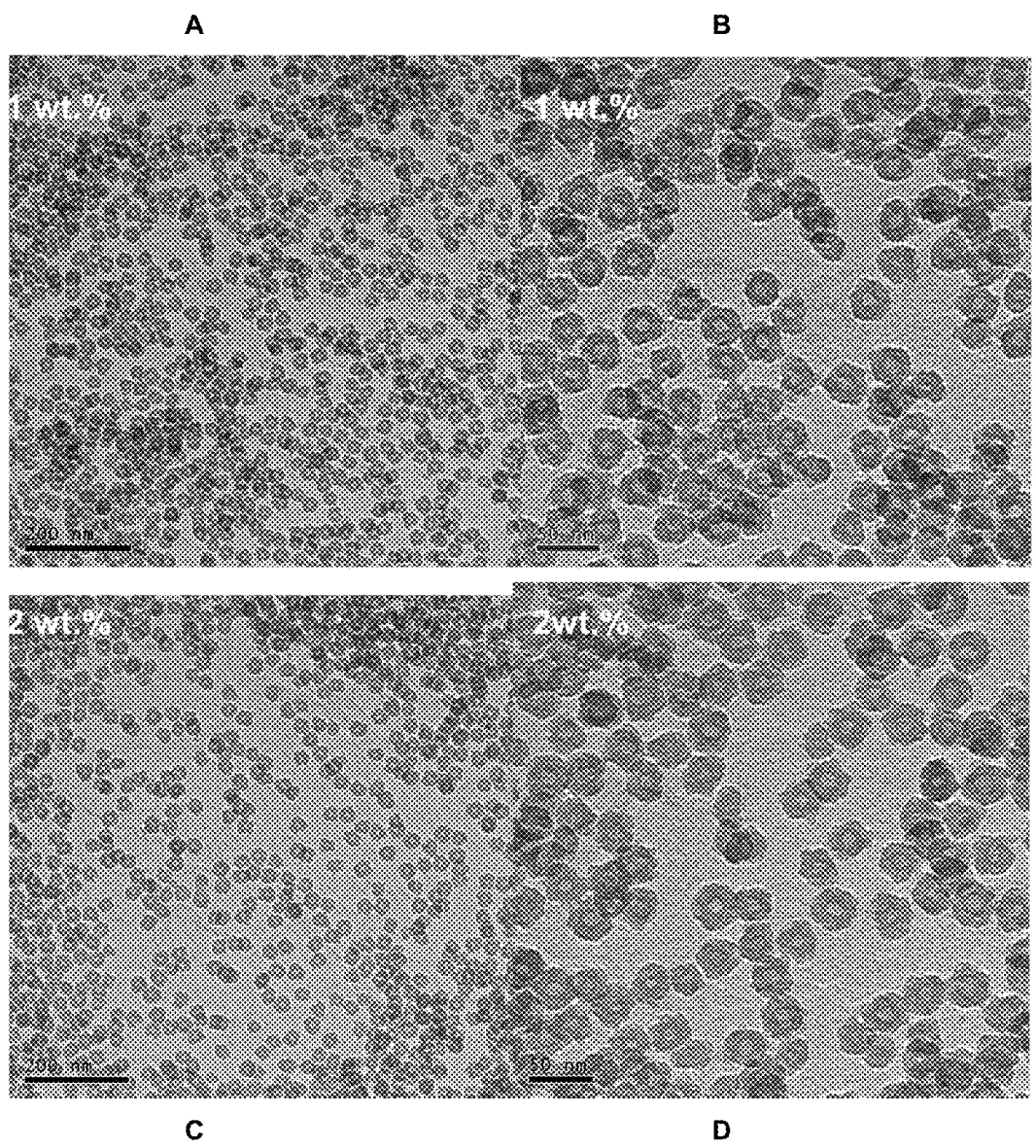

FIG. 11 shows TEM images taken after silica deposition using $PDPA_{23}$-$PDMA_{68}$ diblock copolymer micelles with higher copolymer concentrations, wherein copolymer-silica core-shell nanoparticles were obtained by stirring a mixture containing 1.0 ml of either 1 wt. % or 2 wt. % aqueous solutions of copolymer micelles 50% quaternised with iodomethane [with respect to the PDMA chains only] with either 116 mg or 232 mg of TMOS at 20° C. for 20 minutes at pH 7.2, then diluting the particles with 40 ml ethanol and centrifuging at 16,000 rpm for 30 minutes, and finally redispersing in ethanol with the aid of an ultrasonic bath. This centrifugation-redispersion cycle was repeated to ensure removal of excess TMOS and unreacted silicic acid oligomers.

Figure 12:
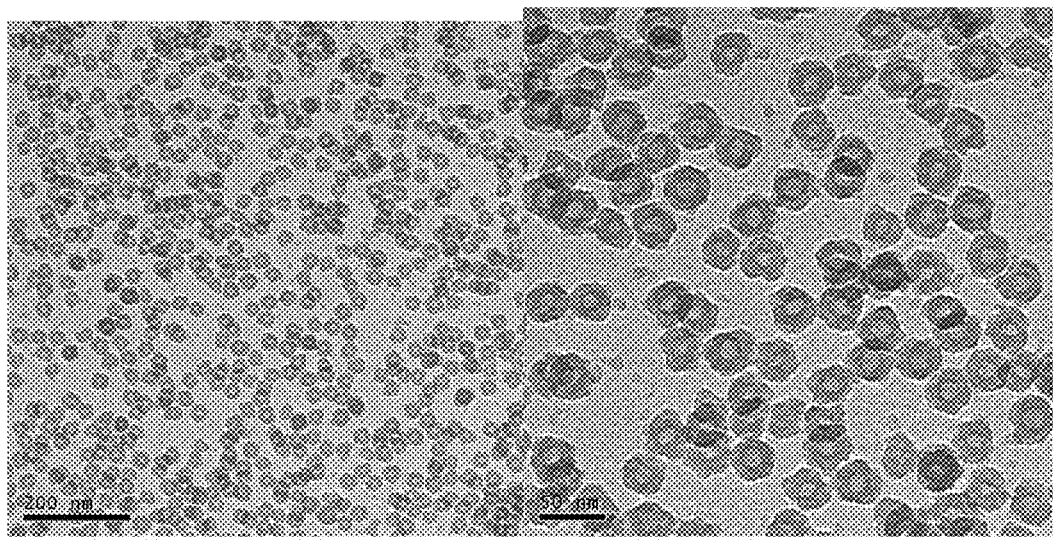

FIG. 12 presents TEM images from silica deposition processes with $PDPA_{23}$-$PDMA_{68}$ diblock copolymer micelles after much longer deposition times, wherein copolymer-silica core-shell nanoparticles were obtained by stirring a mixture containing 2.0 ml of a 0.25 wt. % aqueous solution of copolymer micelles 50% quaternised with iodomethane [with respect to the PDMA chains] with 58 mg of TMOS at 20° C. for 8 hours at pH 7.2, and then subjecting the particles to two ethanol washing and centrifugation cycles (16,000 rpm, 30 minutes).

Figure 13:
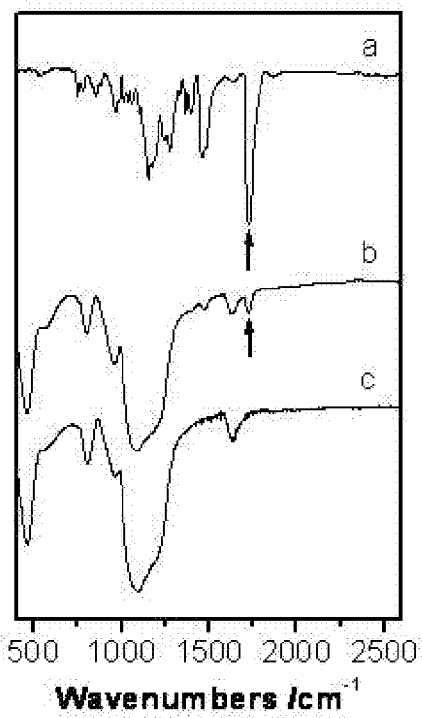

FIG. 13 illustrates FT-IR spectra recorded for: (a) the precursor $PDPA_{23}$-$PDMA_{68}$ diblock copolymer; (b) copolymer-silica core-shell nanoparticles obtained after silica deposition onto shell crosslinked micelles obtained from the $PDPA_{23}$-$PDMA_{68}$ diblock copolymer (target degree of crosslinking=30% using BIEE) under the stated conditions (see FIG. 3A); and (c) hollow silica nanoparticles obtained after pyrolysis of the copolymer by calcination at 800° C.; the FT-IR spectrum of the copolymer-silica core-shell nanoparticles contains IR bands that are characteristic of both the silica network (1080 $cm^{-1}$, multiplet corresponding to Si—O stretching; 950 $cm^{-1}$, Si—OH vibration mode; 800 $cm^{-1}$, Si—O—Si bending; 470 $cm^{-1}$, Si—O bending) and also the copolymer (the carbonyl ester stretch at 1730 $cm^{-1}$); this latter carbonyl band disappears after calcination of the copolymer, as expected, suggesting the formation of hollow silica particles, an eventuality which is confirmed by the results of TEM studies.

Figure 14:
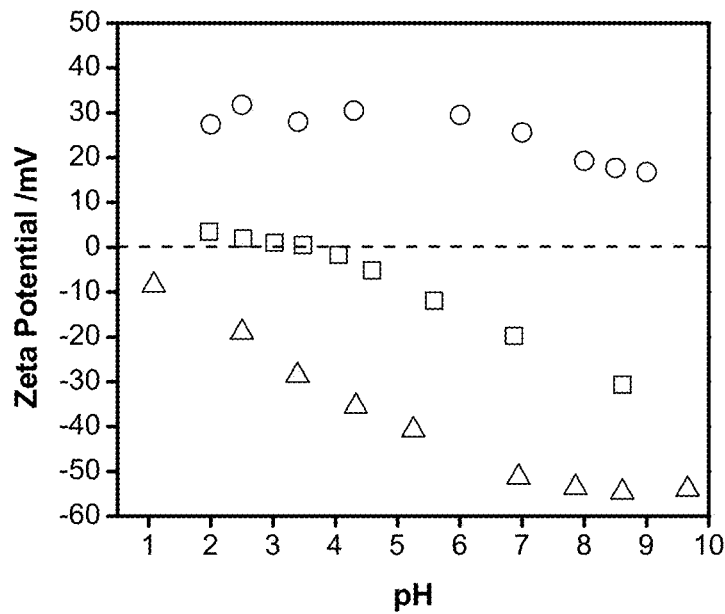

FIG. 14 shows zeta potential vs. pH curves obtained for the original SCL micelles prepared from the $PDPA_{23}$-$PDMA_{68}$ diblock copolymer at a target degree of crosslinking of 30% for the PDMA coronal chains (circles) and the final copolymer-silica core-shell particles synthesised using a mixture of 2.0 ml of a 0.25 wt. % SCL micelle solution (target degree of crosslinking=30%) and 2.0 ml TMOS for 40 minutes (squares); for comparative purposes, the zeta potential curve obtained for an ultrafine commercial 20 nm silica sol (Nyacol 2040) is also shown (triangles).

Figure 15:
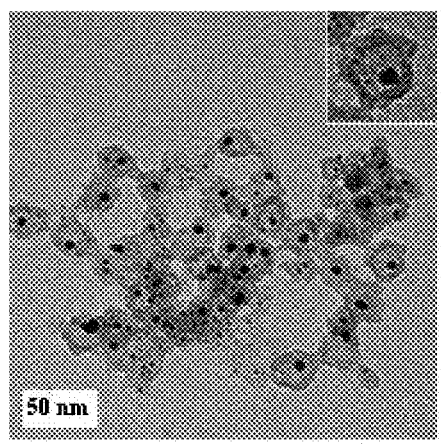

FIG. 15 shows the transmission electron micrograph of Au/silica nanoparticles obtained by protonating the PDPA chains in the cores of the silica-coated micelles using $HAuCl_4$, followed by in situ reduction using $NaBH_4$; this experiment confirms that the PDPA chains remain located within the micelle cores after silica deposition, as expected.

Figure 16:
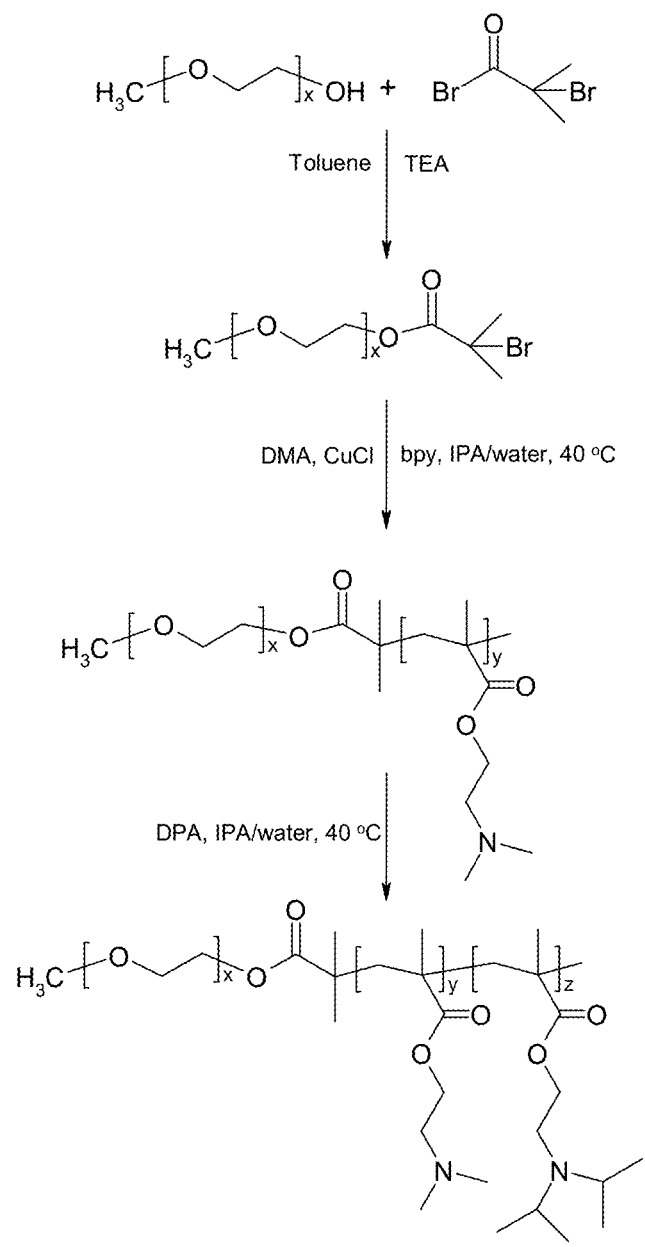

FIG. 16 schematically shows the synthesis of an ABC triblock copolymer based on poly(ethylene oxide) (PEO), PDMA and PDPA, wherein a $PEO_{45}$-$PDMA_{29}$-$PDPA_{76}$ triblock copolymer was synthesized by Atom Transfer Radical Polymerisation (ATRP) using a PEO-based macro-initiator ($PEO_{45}$-Br macro-initiator), via a $PEO_{45}$-$PDMA_{29}$ diblock copolymer.

Figure 17:
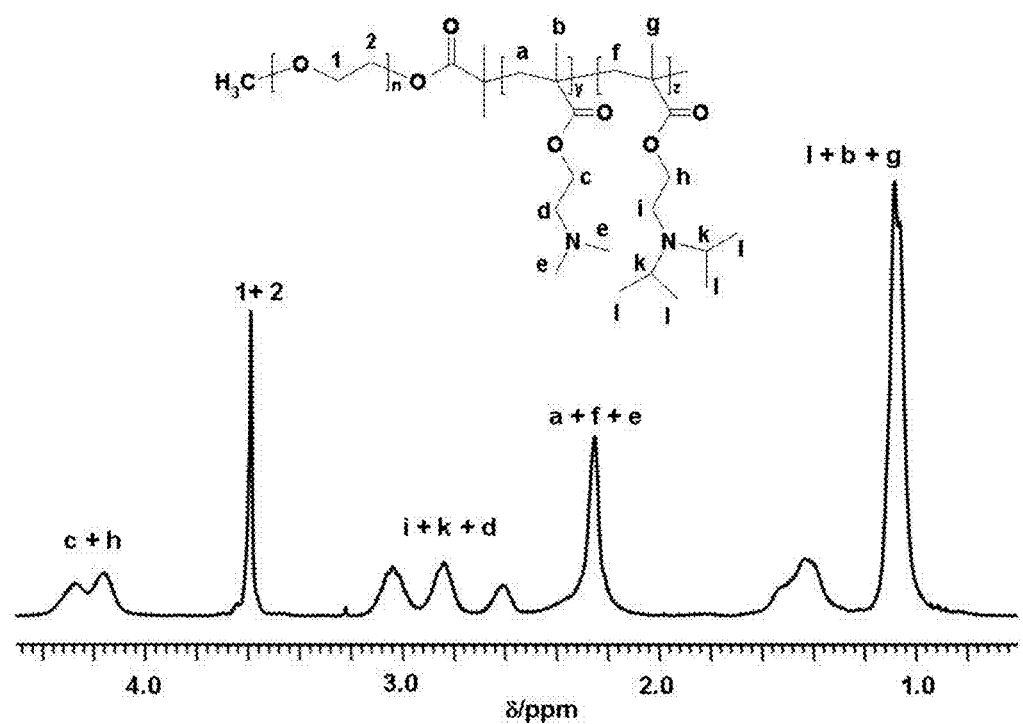

FIG. 17 shows the $^1H$ NMR spectrum of the $PEO_{45}$-$PDMA_{29}$-$PDPA_{76}$ triblock copolymer recorded in $d_5$-pyridine.

Figure 18:
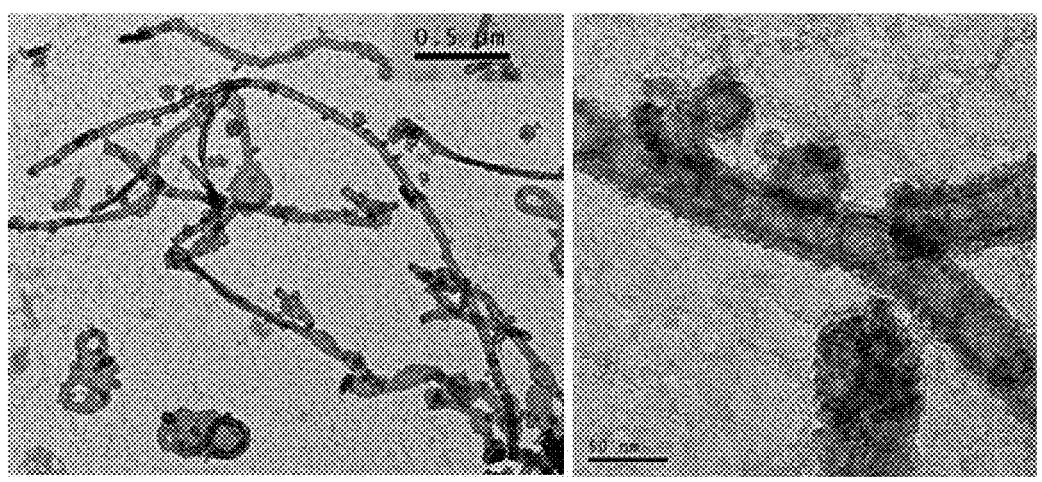

FIG. 18 presents TEM images for silica rods wherein silica deposition was performed at 1.0% copolymer concentration, the resulting silica rods being easily (re)dispersed by ultrasonication.

Figure 19:
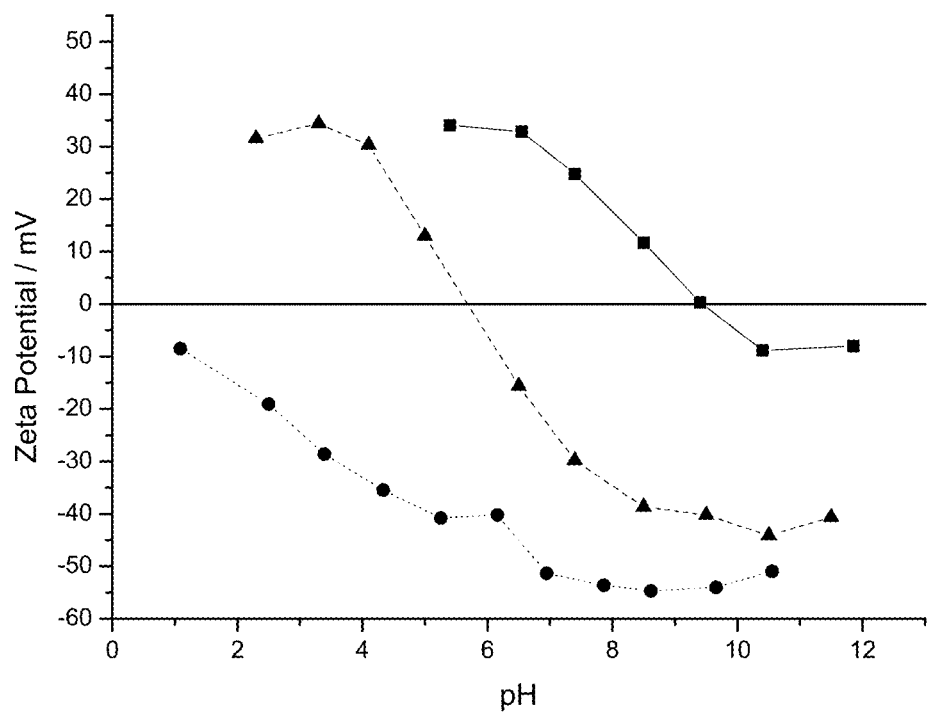

FIG. 19 illustrates comparative zeta potential vs. pH curves obtained for the original copolymer rods prepared from the $PEO_{45}$-$PDMA_{29}$-$PDPA_{76}$ triblock copolymer (shown as squares), and the final silica rods synthesised using a mixture of 1.0 ml of a 1.0 wt. % copolymer micelle solution and 0.20 g TMOS for 20 min (shown as triangles); for comparative purposes, the zeta potential curve obtained for an ultrafine commercial 20 nm silica sol (Nyacol 2040) is also shown (as circles).

Particularly favourable results have been achieved with compositions based on selectively quaternised non-crosslinked and shell crosslinked micelles derived from tertiary amine methacrylate-based block copolymers, a specific example being poly[2-(diisopropylamino)ethyl methacrylate)-block-2-(dimethylamino)ethyl methacrylate] (PDPA-PDMA), and such materials have proved to be particularly successful when used as templates for the biomimetic formation of well-defined copolymer-silica nanoparticles of less than 50 nm diameter. Diblock copolymer micelles comprising either partially or fully quaternised poly(2-(dimethylamino)ethyl methacrylate) (PDMA) coronas and hydrophobic poly(2-(diisopropylamino)ethyl methacrylate) (PDPA) cores in particular have been used as nano-sized templates for the deposition of silica from aqueous solution under mild conditions, i.e. at pH 7.2 and 20° C.

PDPA-PDMA diblock copolymers of this type are relatively easy to synthesise over a range of block compositions and copolymer molecular weights using any suitable method such as group transfer polymerisation or controlled radical polymerisation. Such diblock copolymers dissolve molecularly in acidic solution due to protonation of both polyamine blocks. On adjustment of the solution pH with aqueous base, micellar self-assembly occurs at around neutral pH; the deprotonated hydrophobic PDPA chains form the micelle cores and the cationic (protonated) PDMA chains form the micelle coronas. Alternatively, and depending upon the precise block composition under investigation and the degree of quaternisation, selected diblock copolymers can be dissolved directly in water at around neutral pH to form well defined micelles.

Both non-crosslinked and SCL micelles of this type can be coated with silica without loss of colloid stability. Silica deposition on the SCL micelles is primarily confined to the cationic PDMA shell, leading to core-shell copolymer-silica nanoparticles with pH-responsive PDPA cores. Moreover, in situ silica deposition effectively stabilises the uncrosslinked PDPA-PDMA micelles, which remain intact on lowering the solution pH, whereas the original PDPA-PDMA micelles are found to dissociate to give individual copolymer chains in acidic solution.

In a further embodiment of the invention, it has been shown that a poly(ethylene oxide)-PDMA-PDEA triblock copolymer facilitates the preparation of highly anisotropic rod-like silica particles.

Shell crosslinking of these micelles can be readily achieved at high dilution using 1,2-bis-(2-iodoethoxy)ethane (BIEE) as a bifunctional quaternising reagent under mild conditions. BIEE quaternises the PDMA chains selectively, leaving the much less reactive PDPA chains untouched.

Figure 1:
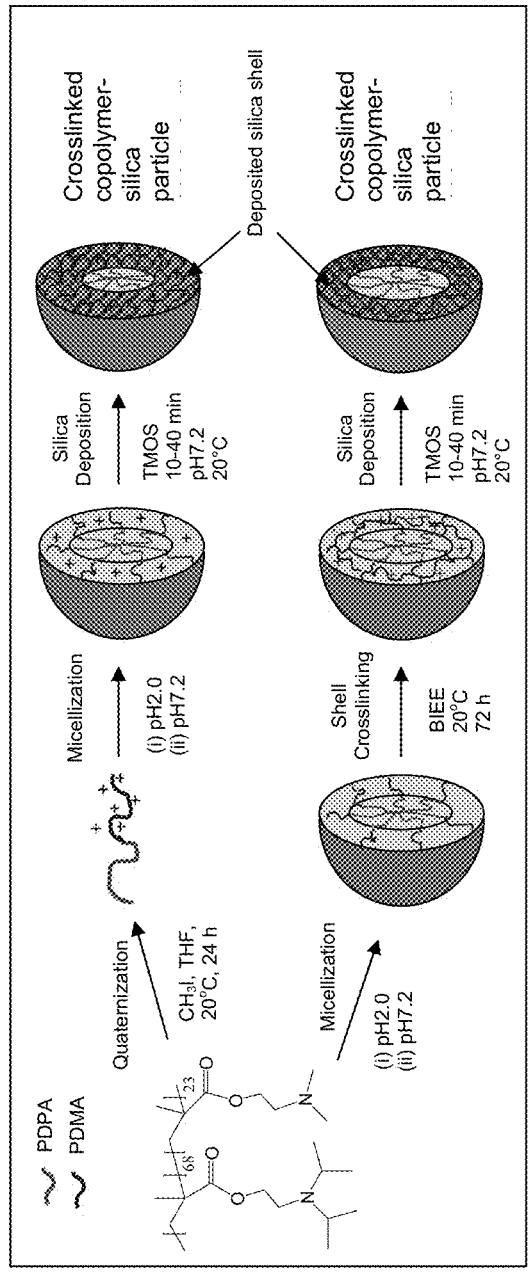

The general approach to the preparation of the compositions according to the first aspect of the invention is shown in FIG. 1, from which it will be gleaned that the thickness of the deposited silica shell differs according to whether or not the copolymer micelle incorporates crosslinking. The degree of quaternisation of the PDMA block can also be an important factor. The PDMA shell has significant cationic character due to either protonation and/or quaternisation, so it can act both as a polymeric catalyst and also as a physical scaffold for silica formation. Tetramethyl orthosilicate (TMOS) was employed as a silica precursor and biomineralization was conducted in aqueous solution at 20° C. at around neutral pH.

Thus, in the first approach, a $PDPA_{23}$-$PDMA_{68}$ block copolymer is either partially or fully quaternised by treatment with iodomethane in tetrahydrofuran at 20° C. for 24 hours, and non-crosslinked micelles are formed by dissolution at pH 2 and adjustment of the pH to 7.2; finally, silica deposition occurs on treatment of the micelles with tetramethyl orthosilicate for 10-40 minutes at room temperature and pH 7.2, resulting in the formation of silica crosslinked nanoparticles having a relatively thick silica shell when using a relatively large excess of TMOS.

Alternatively, micelles are formed by dissolution of the $PDPA_{23}$-$PDMA_{68}$ block copolymer at pH 2 and adjustment of the pH to 7.2, and the micelles are then shell crosslinked by quaternisation by treatment with 1,2-bis-(2-iodoethoxy) ethane (BIEE) at 20° C. for 72 hours; silica deposition is then carried out by treatment of the crosslinked micelles with tetramethyl orthosilicate for 10-40 minutes at room temperature and pH 7.2, resulting in the formation of silica nanoparticles having a relatively thin silica shell when using a relatively large excess of TMOS.

Initially, the present inventors carried out silica deposition using non-crosslinked micelles prepared directly from the $PDPA_{23}$-$PDMA_{68}$ copolymer precursor as templates. Dynamic light scattering (DLS) studies indicated an intensity-average diameter of 37 nm at 25° C. for these micelle templates. At pH 7.2 the PDMA chains in the micelle shell are approximately 50% protonated, and therefore have appreciable cationic character.[24]

Silicification of the said micelles was achieved by mixing 2.0 ml of an aqueous micelle solution (0.25 w/v % at pH 7.2) with 1.0 ml tetramethyl orthosilicate, and then stirring the initially heterogeneous solution under ambient conditions for 20 minutes. The silica-coated nanoparticles thus obtained were washed with ethanol, then subjected to three centrifugation/redispersion cycles at 16,000 rpm for 5 minutes. Redispersal of the sedimented nanoparticles was subsequently achieved with the aid of an ultrasonic bath.

Figure 2:
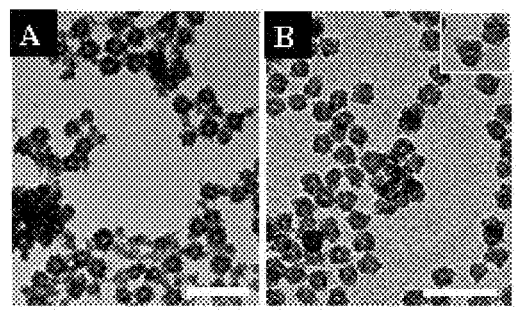

Thermogravimetric analyses of the product indicated that the mean diblock copolymer content of the silica nanoparticles was about 15% by mass. A typical Transmission Electron Micrograph (TEM) image obtained for these TMOS-treated micelles is shown in FIG. 2A. The formation of templated silica nanoparticles with core-shell structures is clearly observed, since the silica/PDMA hybrid shell is more electron-dense than the PDPA chains within the micelle cores. These nanoparticles have a number-average diameter of around 35 nm, which is in reasonably good agreement with the dimensions of the precursor micelles. However, in addition to the formation of templated silica nanoparticles, some ill-defined, non-templated silica structures are also observed in FIG. 2A, indicating that the silica formation is not particularly well controlled in this case. Ideally, silica formation should occur exclusively on the cationic copolymer micelles, rather than in bulk solution.

Improved control over silica deposition was, however, achieved when employing quaternised polymers. Initial trial experiments were conducted using PDMA homopolymer, and it was found that on mixing 1.0 ml tetramethyl orthosilicate and 1.0 ml aqueous PDMA homopolymer solution (concentration of DMA repeat units, [DMA]=0.064 M) at pH 7.2 and 20° C., the initially heterogeneous solution became homogeneous after continuous stirring for 15 minutes (hydrolysis of TMOS, which produces silicic acid, allows the system to become homogeneous). By way of contrast, for 50% and 100% quaternised PDMA homopolymers under identical conditions, the corresponding times required for the reaction solutions to become homogeneous were 25 minutes and 50 minutes, respectively. This suggests that quaternised PDMA chains catalyse slower, and therefore perhaps more controlled, hydrolysis of the TMOS precursor.

These experiments with PDMA homopolymer suggested that well-controlled silica deposition might be achieved using partially or fully quaternised $PDPA_{23}$-$PDMA_{68}$ copolymer micelles as templates. Thus, experiments were conducted wherein selective quaternisation of DMA residues was achieved using iodomethane under mild conditions. A 0.25 wt. % aqueous solution of $PDPA_{23}$-$PDMA_{68}$ copolymer micelles in which the PDMA chains were 50% quaternised had an intensity-average diameter of 29 nm at pH 7.2, as indicated by Dynamic Light Scattering (DLS). Tetramethyl orthosilicate (1.0 ml) was added to 2.0 ml of the aqueous micelle solution at 20° C., and silica deposition was allowed to continue for 20 minutes, with continuous stirring, prior to isolation via centrifugation.

Figure 4:
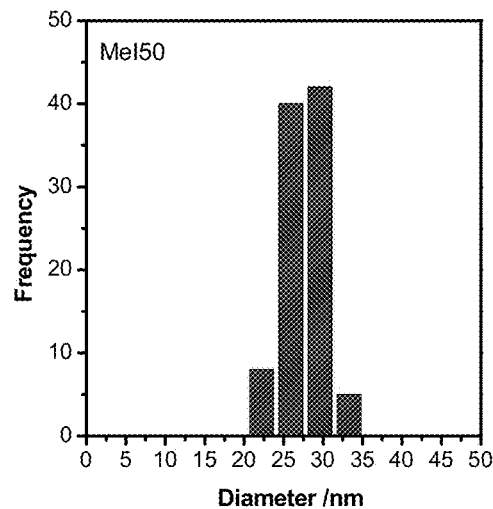

TEM images of the purified core-shell copolymer-silica nanoparticles obtained are shown in FIG. 2B. Core-shell nanostructures were clearly observed, with a number-average diameter of 28±3 nm. DLS studies indicated an intensity-average diameter of 34 nm and a relatively narrow size distribution, as illustrated in FIG. 4. In contrast to the results obtained for the non-quaternised diblock precursor, there was no evidence for non-templated silica structures in this case, suggesting that secondary nucleation had been minimised.

Figure 5:
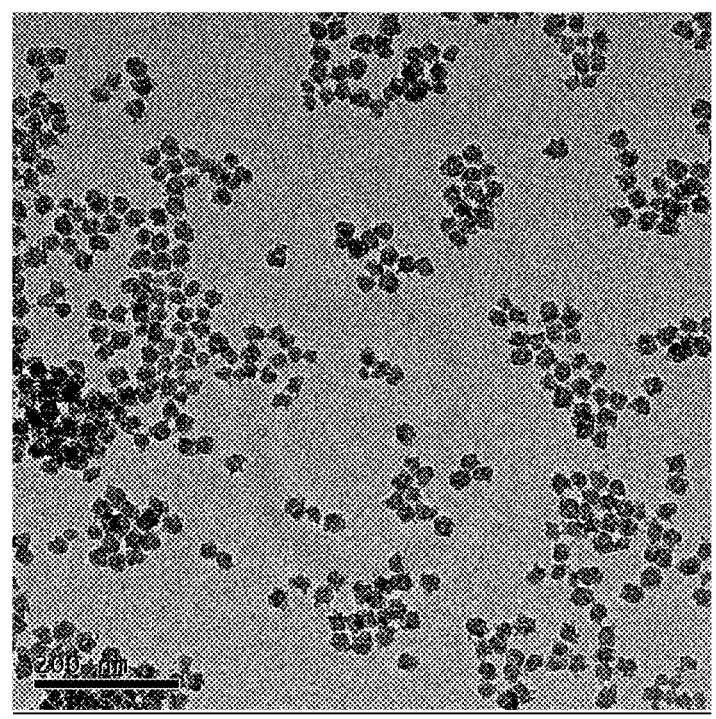

TEM results obtained using micelles with 100% quaternised PDMA blocks are shown in FIG. 5, from which it is apparent that there is little or no evidence of the formation of a copolymer core, thus confirming that partially quaternised copolymers are a particularly preferred embodiment of the present invention. Thermogravimetric analyses, however, indicated that the mean diblock copolymer contents of the silica nanoparticles derived from micelles with 50% and 100% quaternised PDMA blocks were about 18% and 16% by mass, respectively. Thus, quaternisation of the PDMA chains does appear to be beneficial for well-controlled silica deposition. Moreover, these quaternised micelles produced hybrid nanoparticles with much thicker, more well defined silica shells relative to those obtained using non-quaternised copolymer micelles (see FIG. 2A) under the same biomineralisation conditions.

Figure 9:
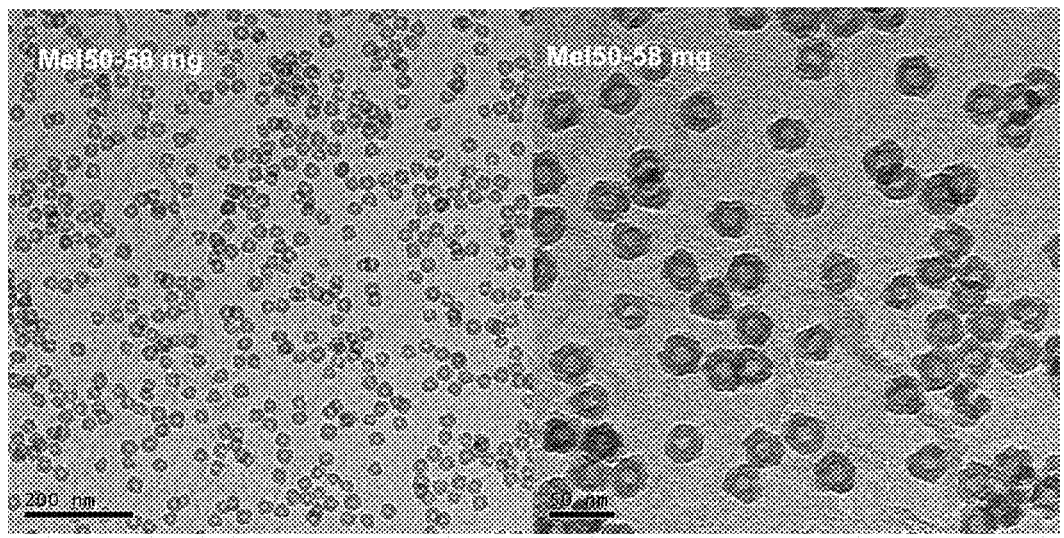
FIG. 9 shows Transmission Electron Micrographs of core-shell copolymer-silica nanoparticles obtained by stirring a mixture containing 2.0 ml of a 0.25 wt. % aqueous solution of partially quaternised (50% iodomethane-quaternised with respect to the PDMA shell) copolymer micelles and either (images A, B) 58 mg or (images C, D) 116 mg of TMOS at 20° C. for 20 minutes at pH 7.2.
Figure 9:
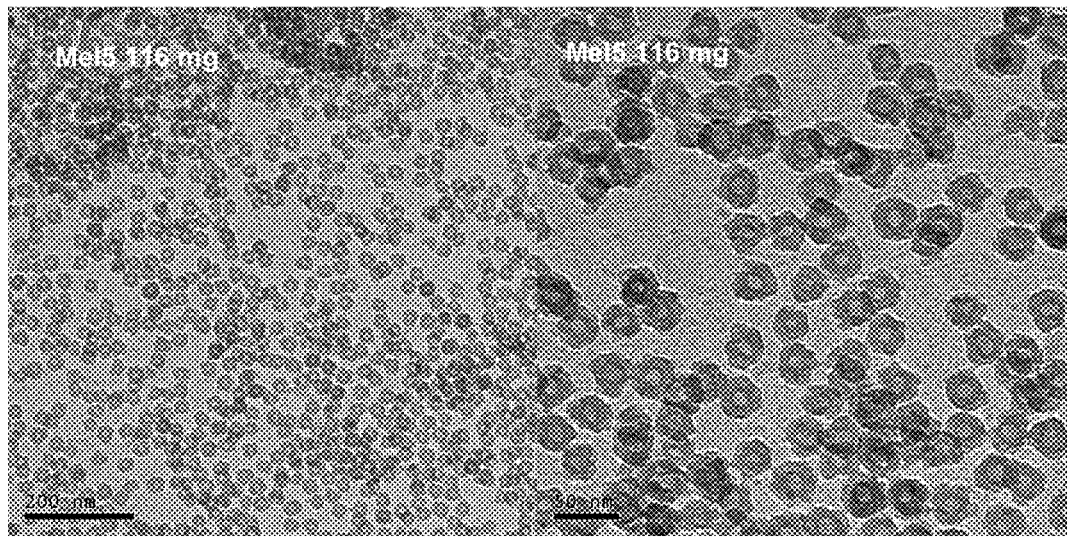

The present inventors have also established that the nanostructure of these copolymer-silica core-shell particles can be simply controlled by tuning the amount of TMOS used for silica deposition. Thus, for example, silica particles with thin shells and large copolymer cores were obtained when using lower levels of TMOS. Well-defined silica particles with a number-average diameter of around 26 nm (see FIG. 9A/9B) were formed by stirring a mixture of 58 mg TMOS with 2 ml of a 0.25 w/v % solution of 50% quaternised copolymer micelles for 20 minutes. As shown in Table 1, thermogravimetric analysis of the product indicated that the mean copolymer content of these core-shell copolymer-silica particles was about 28% by mass, indicating a silica conversion of about 58%. Such particles have much thinner silica shells and larger copolymer cores. Moreover, colloidal stability was maintained even when the reaction time was increased from 20 minutes to 8 hours when using this reduced amount of TMOS (see FIG. 12A/12B). The results obtained when increasing the quantity of TMOS in the above synthesis to 116 mg are shown in FIG. 9C/9D. Again, there is no evidence for non-templated silica (such as that observed in FIG. 2B), indicating efficient templating of these silica nanostructures. Further thermogravimetric analyses indicated that these core-shell copolymer-silica nanoparticles had lower copolymer contents (23%) compared to the core-shell copolymer-silica nanoparticles shown in FIG. 9A/9C (28% copolymer content). This indicates that higher levels of TMOS lead to more silica deposition under otherwise identical conditions.

Figure 6:
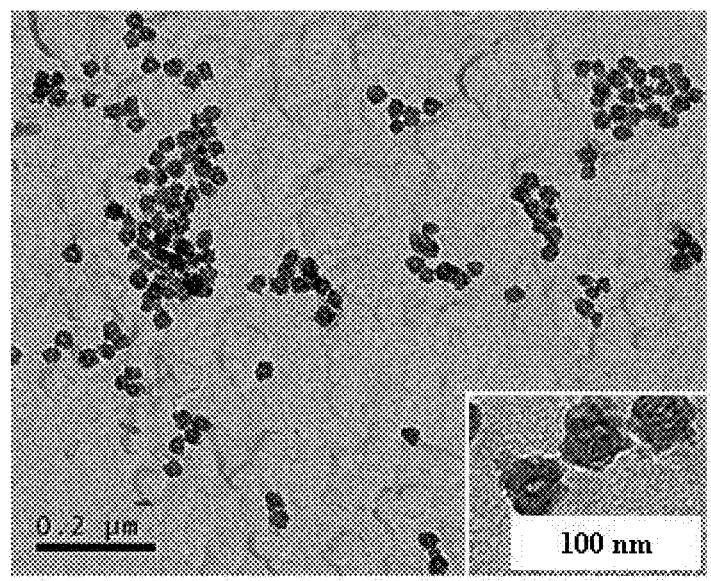
Figure 7:
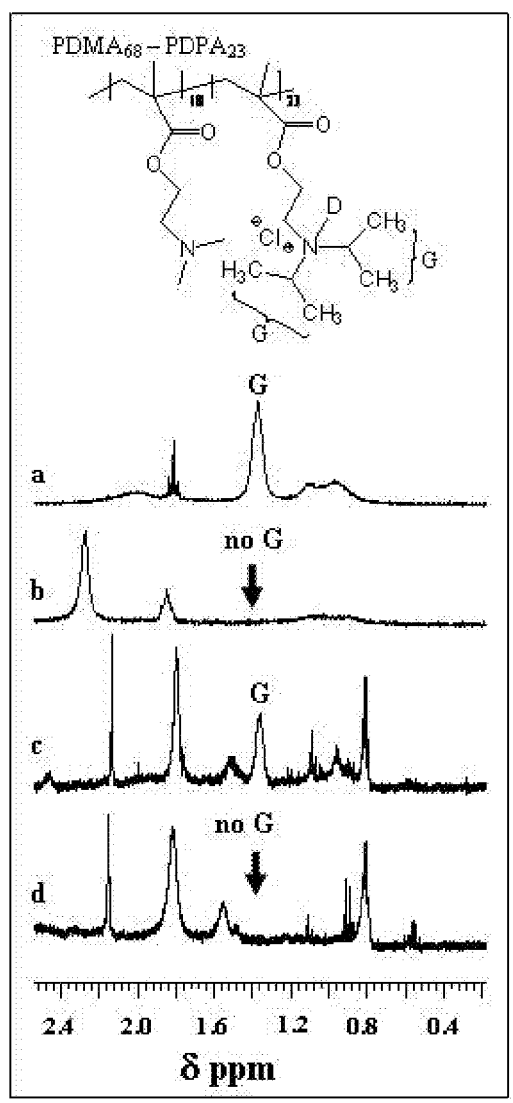

TEM studies provided further evidence of efficient micelle crosslinking via biomineralisation. As shown in FIG. 2B (see inset) and FIG. 6, the silica crosslinked micelles retain their spherical core/shell structures after direct dispersion and drying at pH 2. $^1$H NMR studies of the core-shell copolymer-silica nanoparticles at pH 2 produced a signal at δ 1.3-1.4 due to the protonated PDPA chains (see FIG. 7). When the solution pH was increased to pH 7, however, this signal disappeared as the PDPA chains became deprotonated and hence hydrophobic. Thus, these spectroscopic studies confirmed that the PDPA chains in the micelle cores are pH-responsive (i.e. they can become hydrophilic at low pH and hydrophobic at high pH), and this further illustrates the potential use of these new core-shell copolymer-silica nanoparticles in encapsulation/controlled release applications.

Typically, shell crosslinking is conducted at high dilution (normally less than 0.5 wt. % copolymer micelles) in order to avoid inter-micelle fusion. However, micelle crosslinking by biomimetic silica deposition can be successfully performed at somewhat higher concentrations. Thus, as shown in FIG. 11A/11B, the mixing of 1 ml of a solution of 1.0 w/v % copolymer micelles (50% quaternised with respect to the PDMA shell) with 116 mg TMOS for 20 minutes produced well-defined hybrid copolymer-silica core-shell particles with a number average diameter of about 26 nm. Similar-sized particles were also obtained using 2.0 w/v % copolymer micelles (see FIG. 11C/11D). Thermogravimetric analyses (Table 1) indicated that the mean copolymer contents of the copolymer-silica core-shell particles shown in FIGS. 11A/11B and 11C/11D were about 20 and 22% by mass, respectively, indicating silica conversions of 87 and 78%, respectively. Thus this biomimetic approach to SCL micelles by silica deposition appears to be notably efficient, and to offer particular advantages in terms of mild reaction conditions, fast reaction times and relatively inexpensive reagents when compared with the methods of the prior art.

The present inventors also prepared SCL micelles by selective quaternisation and crosslinking of the PDMA chains using 1,2-bis-(2-iodoethoxy)ethane, and evaluated the resulting cationic micelles as templates for silica deposition. The target degree of crosslinking for the PDMA coronal chains was 30 mol %. DLS studies conducted at 25° C. indicated an intensity-average micelle diameter of 37 nm for the precursor SCL micelles.

Figure 3:
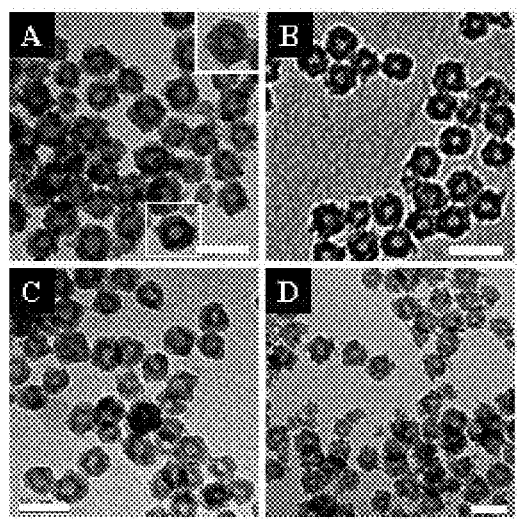
Figure 8:
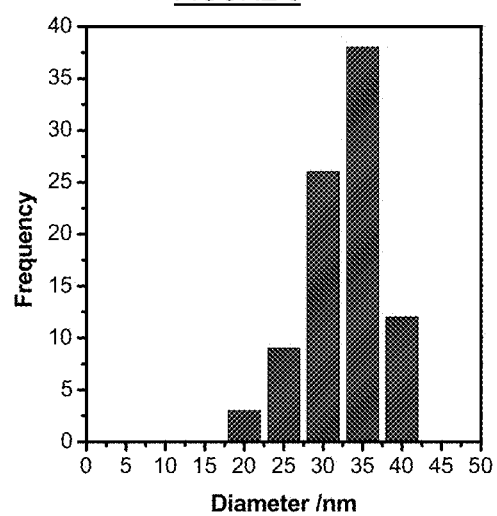
FIG. 8 shows the TEM particle size distribution of the hybrid silica nanoparticles (as shown in FIG. 3A; prepared using SCL micelles at a target degree of crosslinking for the PDMA chains of 30%); these core-shell copolymer-silica nanoparticles have a number-average diameter of 32±5 nm and an intensity-average diameter of 35 nm from DLS measurements.

Biomineralisation was performed using tetramethyl orthosilicate under the same conditions as those employed for non-crosslinked micelles. FIG. 3A shows a typical TEM image of the resulting silica nanoparticles. Their intensity-average and number-average diameters from DLS and TEM are 35 nm and 32±5 nm (see FIG. 8), respectively, which are in reasonably good agreement with the values obtained for the SCL micelle precursor. Furthermore, their core-shell structure is also clearly evident. For example, the silica nanoparticle indicated by the lower white square in FIG. 3A has a PDPA core of approximately 14 nm and a silica/PDMA hybrid shell thickness of around 11 nm. Biomineralisation studies with SCL micelles prepared at a target degree of crosslinking of 50% produced similar results, as shown in FIG. 3B. Compared to the silica nanoparticles prepared using non-crosslinked micelles (FIG. 2A), the silica particles obtained from SCL micelle precursors have larger cores and thinner shells. In addition, there is no evidence for non-templated silica within the dispersion, indicating that silica deposition is again well-controlled.

Silica deposition was also performed at lower levels of TMOS. Thus, on mixing a 2 ml aliquot of a 0.25 w/v % copolymer micelle solution (50% target degree of crosslinking using BIEE) with 58 mg TMOS for 20 minutes, silica deposition led to aggregation, rather than a colloidally stable dispersion. TEM studies indicated the formation of core-shell silica particles of about 17 nm, as well as interconnected, fused primary particles (see FIG. 10A/10B). Thermogravimetric analyses (see Table 1) indicated a mean copolymer content of around 30% by mass, indicating a silica conversion of approximately 50%. The formation of silica nanoparticles was much improved by using a slight excess of TMOS under the same conditions. Hence, mixing 2 ml of a 0.25 w/v % copolymer micelle solution (50% target degree of crosslinking using BIEE) with 116 mg TMOS for 20 minutes produced a colloidally stable dispersion, as judged by visual inspection. As shown in FIG. 10C/10D, hybrid copolymer-silica particles with a number-average diameter of about 20 nm were obtained. Thermogravimetric analyses indicated a mean copolymer content of about 24% by mass, indicating a silica conversion of around 35%.

Silica deposition can be also controlled using SCL micelles under initially homogeneous conditions. Thus, a 2.0 ml aliquot of a 0.25 wt. % SCL micelle solution was added to a mixture of 2.0 ml methanol and 2.0 ml tetramethyl orthosilicate, wherein the methanol acted as a co-solvent and ensured that the TMOS was miscible with the aqueous phase from the beginning of the reaction. After continuing silica deposition for 40 minutes, TEM studies of the obtained product, as illustrated in FIG. 3C, confirmed the expected formation of well-defined core-shell copolymer-silica nanoparticles. Even after continuing the treatment for 120 minutes, however, no evidence for non-templated silica nanostructures was observed, as shown in FIG. 3D.

The SCL micelle-derived core-shell copolymer-silica nanoparticles shown in FIG. 3A were further characterised using thermogravimetric analyses, FT-IR spectroscopy and aqueous electrophoresis. Thermogravimetric analyses indicated that the mean copolymer content of the copolymer-silica particles was about 19% by mass, whilst the FT-IR studies, illustrated in FIG. 13, confirmed silica formation, since bands were observed at 1080, 950, 800 and 470 cm$^{-1}$ for these particles, due to the presence of the inorganic component; these bands were found to be absent in the spectra obtained for the copolymer micelles prior to biomineralisation. After calcination at 800° C., the characteristic bands at 1726 cm$^{-1}$, associated with the pyrolysed copolymer, completely disappeared, whilst those bands assigned to the thermally-stable silica were still observed.

TEM studies indicated that the calcined copolymer-silica particles became hollow silica particles after pyrolysis of the organic component. Zeta potential measurements also supported the deposition of silica within the coronal layer of the copolymer micelles, as shown in FIG. 14. The precursor SCL micelles (having a target degree of crosslinking for the PDMA chains of 30%) had positive zeta potentials over the whole pH range investigated, due to their cationic PDMA shells. However, the silica-coated micelles exhibited negative zeta potentials over a wide pH range, with an isoelectric point at around pH 3.3. This latter behaviour is similar to that found for aqueous colloidal silica sols (see FIG. 14) and is, therefore, consistent with the SCL micelles becoming coated with a silica overlayer.

The inventors also attempted the deposition of gold nanoparticles within these hybrid copolymer-silica particles. In order to achieve this, HAuCl$_4$ was initially used to protonate the weakly basic PDPA chains within the cores of the nanoparticles. Then, the $AuCl_4^-$ counter-ions associated with the protonated PDPA chains were reduced in situ to produce zero-valent gold nanoparticles, using $NaBH_4$ as a reducing agent. The colour of the copolymer-silica hybrid nanoparticles changed from white to wine red after the reduction step, indicating the formation of nano-sized gold sols. TEM observations, as illustrated in FIG. 15, provided evidence for the generation of gold sols within the cores of the copolymer-silica nanoparticles, although some disruption of the silica shells was also apparent. The experiment also provided direct evidence for the presence of the PDPA chains within the cores of the hybrid copolymer-silica particles.

Thus, the potential for encapsulation of other species, such as quantum dots or biologically-active molecules, is clearly illustrated. Indeed, as a consequence of their well-defined nanostructures, these hybrid copolymer-silica nanoparticles have potential applications in biolabeling, biodiagnostics, targeted drug delivery, solubilization, catalysis and imaging, and as fillers and coatings.

The fact that mild conditions, fast reaction times, and accessible reagents can be utilised herein may offer clear advantages when preparing commercially applicable processes. In addition, the ability to control the size and/or properties of the particles offers benefits.

The use of silica also offers particular advantages in terms of the potential applications of the materials of the invention. Thus, since silica is usually considered to be a 'food-grade' material, these new particles have potential applications in food manufacturing.

It is clear from the work of the inventors that the effect of varying the degree of quaternisation and shell crosslinking of the diblock copolymer templates under investigation has a significant effect on the nature of the silica nanoparticles that are produced during in situ silica biomineralisation, since either solid spheres (with no cavities), or structured core-shell spheres with thin shells, or structured core-shell spheres with thick shells can be obtained, depending on the precise nature of the copolymer micelles.

The core-shell copolymer-silica nanoparticles of the present invention are somewhat larger than those of the prior art (30 nm vs. 10 nm), and this should allow higher loading capacities. The core-shell nature of the hybrid copolymer-silica particles has been clearly illustrated by TEM studies, and these results have been corroborated by small angle x-ray scattering studies (SAXS). The mean wall thicknesses obtained by TEM and SAXS are in good agreement.

Perhaps the most significant advantage of the present invention, however, lies in the fact that the core-forming PDPA block in the claimed compositions is pH-responsive, and this offers the possibility of pH-triggered release of hydrophobic actives from the cores of the hybrid copolymer-silica nanoparticles.

The use of ABC triblock copolymers has found particular success in the preparation of predominantly anisotropic rod-like copolymer-silica particles, and the said nanorods should allow zero-order diffusional release to be achieved. The synthesis of said nanorods is illustrated in FIG. 16 wherein a poly(ethylene oxide)-based macroinitiator ($PEO_{45}$-Br) is firstly reacted with 2-(dimethylamino)ethyl methacrylate (DMA) in the presence of copper(I) chloride, then the product is further reacted with 2-(diisopropylamino)ethyl methacrylate (DPA). The obtained copolymer was characterised by GPC and $^1$H NMR, and the results are summarised in Table 2 and FIG. 17, which shows the $^1$H NMR spectrum of the triblock copolymer recorded in $d_5$-pyridine.

This copolymer was designed to self-assemble into colloidal micellar aggregates with PDPA cores, PEO coronas and PDMA inner shells. Since the PDMA block has a $pK_a$ of around 7.0, these residues are approximately 50% protonated at pH 7.2. Thus, silica deposition was expected to occur exclusively within the cationic PDMA inner shells, with the coronal PEO blocks imparting steric stabilization. Thus, it is believed that silica deposition can be performed at relatively high copolymer concentrations without inducing particle fusion.

Silica deposition was performed at 1.0% copolymer concentration to produce the anisotropic rod-like copolymer-silica particles, which were easily (re)dispersed by ultrasonication. The resulting silica rods were characterized using TEM, thermogravimetric analyses, FT-IR spectroscopy and zeta potential measurements. FIG. 18 shows a representative TEM image of the silica rods. FT-IR studies confirmed silica formation and polymer encapsulation, since bands were observed at 1080, 950, 800 and 470 $cm^{-1}$ due to the inorganic component, and at 1726 $cm^{-1}$ due to the carbonyl ester stretch of polymer for these silica rods. Thermogravimetric analyses indicated that the mean copolymer content of these hollow silica rods was about 26% by mass and, as shown in FIG. 19, zeta potential measurements indicated the successful coating of silica onto the copolymer micelles.

The invention will now be further illustrated, though without in any way limiting the scope of the disclosure, by reference to the following examples.

EXAMPLES

Example 1

$PDPA_{23}$-$PDMA_{68}$ diblock copolymer was synthesised by sequential monomer addition using group transfer polymerisation according to Chem. Commun. 1997, 671-672. Gel permeation chromatography analysis indicated an $M_n$ of 18,000 and an $M_w/M_n$ of 1.08 using a series of near-monodisperse poly(methyl methacrylate) calibration standards. The mean degrees of polymerisation of the PDPA and PDMA blocks were estimated to be 23 and 68, respectively, using $^1$H NMR spectroscopy.

Non-crosslinked micelles of the $PDPA_{23}$-$PDMA_{68}$ diblock copolymer (degree of quaternisation=0%) were prepared by molecular dissolution at pH 2, followed by adjusting the solution pH to pH 7.2 using NaOH. Dynamic light scattering (DLS) studies at 25° C. indicated an intensity-average micelle diameter of 37 nm for a 0.25 wt. % copolymer micelle solution at pH 7.2.

Silicification of the said micelles was achieved by mixing 2.0 ml of an aqueous micelle solution (0.25 w/v % at pH 7.2) with 1.0 ml tetramethyl orthosilicate, and then stirring the initially heterogeneous solution under ambient conditions for 20 minutes. The hybrid core-shell copolymer-silica nanoparticles thus obtained were washed with ethanol, then subjected to three centrifugation/redispersion cycles at 16,000 rpm for 5 minutes. Redispersal of the sedimented core-shell copolymer-silica nanoparticles was subsequently achieved with the aid of an ultrasonic bath.

Example 2

$PDPA_{23}$-$PDMA_{68}$ diblock copolymer was synthesised by sequential monomer addition using group transfer polymerisation as in Example 1.

Partial quaternisation of the PDMA block (targeting a degree of quaternisation of either 50% or 100%) using iodomethane was conducted in THF for 24 hours, as described in *Macromolecules* 2001, 34, 1148-1159.

Non-crosslinked micelles prepared using either 50% or 100% quaternised $PDPA_{23}$-$PDMA_{68}$ diblock copolymers were also prepared by pH adjustment, as described in Example 1. DLS studies conducted at pH 7.2 indicated intensity-average diameters of 29 nm and 26 nm for 0.25 wt. % aqueous solutions of 50% and 100% quaternised copolymer micelles, respectively.

Tetramethyl orthosilicate (1.0 ml) was added at 20° C. to 2.0 ml of a 0.25 wt. % aqueous solution of $PDPA_{23}$-$PDMA_{68}$ copolymer micelles in which the PDMA chains were 50% quaternised, and silica deposition was allowed to continue for 20 minutes, with continuous stirring, prior to isolation via centrifugation.

DLS studies on the hybrid core-shell copolymer-silica nanoparticles obtained using the 50% quaternised copolymer precursor indicated an intensity-average micelle diameter of 34 nm at around pH 7.

Example 3

$PDPA_{23}$-$PDMA_{68}$ diblock copolymer was synthesised by sequential monomer addition using group transfer polymerisation, and non-crosslinked micelles of the $PDPA_{23}$-$PDMA_{68}$ diblock copolymer were prepared as described in Example 1.

Shell crosslinking of the coronal PDMA chains was achieved by adding a bifunctional quaternising agent, 1,2-bis-(2-iodoethoxy)ethane (BIEE, 0.15 moles per DMA residue for a target degree of cross-linking of 30%) to a 0.25% $PDPA_{23}$-$PDMA_{68}$ copolymer micelle solution at pH 7.2. Shell crosslinking was carried out at 25° C. for at least 72 hours. After shell crosslinking, DLS studies indicated an intensity-average diameter of 32 nm and TEM studies suggested a number-average diameter of 26 nm for the dried SCL micelles. On adjusting the aqueous SCL micelle solution to pH 2, DLS studies indicated an intensity-average diameter of 45 nm due to swelling of the SCL micelles.

This DLS experiment also confirmed successful shell crosslinking, since the non-crosslinked micelles simply dissociate at low pH to form a molecular solution, because the PDPA chains are highly protonated, and hence no longer hydrophobic, at low pH. In addition, SCL micelles prepared using the 50% quaternised copolymer had an intensity-average diameter of 37 nm at pH 7.2 as indicated by DLS.

Silica deposition was achieved by adding a 2.0 ml aliquot of a 0.25 wt. % SCL micelle solution to a mixture of 2.0 ml methanol and 2.0 ml tetramethyl orthosilicate, wherein the methanol acted as a co-solvent and ensured that the TMOS was miscible with the aqueous phase. After continuing silica deposition for 40 minutes, TEM studies of the obtained product confirmed the formation of well-defined core-shell copolymer-silica nanoparticles, as illustrated in FIG. 3C. Even after continuing the treatment for 120 minutes, however, no evidence for non-templated silica nanostructures was observed, as shown in FIG. 3D.

Example 4

$PEO_{45}$-$PDMA_{29}$-$PDPA_{76}$ triblock copolymer was synthesized by Atom Transfer Radical Polymerisation using a PEO-based macro-initiator by firstly adding the macro-initiator (1.00 g, 0.463 mmol) to a 25 ml one-neck flask, then degassing by three vacuum/nitrogen cycles, followed by the addition of DMA (2.18 g, 13.88 mmol, target DP 30), 2,2'-bipyridine (144.5 mg, 0.925 mmol) and then 3.2 ml of a degassed 95/5 v/v IPA/water mixture. The solution was placed in a 40° C. oil bath and stirred until homogeneous. Copper(I) chloride (45.8 mg, 0.463 mmol) was then added and the reaction was carried out at 40° C. for 3.5 hours under nitrogen with continual stirring. After this time, the DMA monomer conversion reached 96%, as determined by $^1$H NMR spectroscopy.

Thereafter, a mixture of DPA (4.94 g, 23.13 mmol, target DP=50) and 5.0 ml of a 95/5 v/v IPA/water mixture was added. The second-stage polymerization was carried out at 40° C. for 18.5 hours, before being terminated by exposure to air. $^1$H NMR analysis showed that the DPA monomer conversion reached 99%. The copolymer solution was diluted with THF (200 ml) and passed through a silica column to remove the spent catalyst. The copolymer solution was then concentrated under vacuum and the solid copolymer was precipitated into deionized water (100 ml) to remove residual monomer and any unreacted PEO-DMA diblock copolymer. The purified white copolymer was isolated by freeze-drying under vacuum overnight to give an overall yield of 6.1 g (76%).

The micellar rods formed by the $PEO_{45}$-$PDMA_{29}$-$PDPA_{76}$ triblock copolymer were prepared by molecular dissolution at pH 2, followed by adjusting the solution pH to 7.2 using NaOH. The final copolymer concentration was 1.0 wt. %. Silica deposition was achieved by adding excess TMOS (0.20 g; i.e. a TMOS:copolymer mass ratio of 20:1) to 1.0 ml of copolymer solution and silicification was then conducted for 20 minutes at 20° C. and pH 7.2. Silica rods were obtained by washing with ethanol, followed by three centrifugation/redispersion cycles at 13,000 rpm for 15 minutes.

TABLE 1

TGA results of silica synthesized using the $PDPA_{23}$—$PDMA_{68}$ diblock copolymer micelles under various quaternisation conditions at 20° C. and pH 7.2.

| Precursor micelles | MeI(50) | MeI(50) | MeI(50) | BIEE(50) | BIEE(50) | BIEE(50) | MeI(50) | MeI(50) |
|---|---|---|---|---|---|---|---|---|
| Concentrations/wt. % | 0.25 | 0.25 | 0.25 | 0.25 | 0.25 | 0.25 | 1.0 | 2.0 |
| Copolymer/mg | 5 | 5 | 5 | 5 | 5 | 5 | 10 | 20 |
| TMOS/mg | 58 | 116 | 1000 | 58 | 116 | 1000 | 116 | 232 |
| Target polymer content from reaction feeding/wt. % | 18 | 36 | 1.3 | 18 | 36 | 1.3 | 18 | 18 |
| Actual polymer content from TGA/wt. % | 28 | 23 | 18 | 30 | 24 | 19 | 20 | 22 |
| Silica Conversion/% | 56 | 36 | 6 | 51 | 34 | 5 | 87 | 78 |
| Diameters from TEM (nm) | 33 | 33 | 28 | 20 | 23 | 26 | 33 | 35 |

TABLE 2

Summary of molecular weight data obtained for the PEO$_{45}$—Br macro-initiator, PEO$_{45}$—PDMA$_{29}$ diblock precursor and the final PEO$_{45}$—PDMA$_{29}$—PDPA$_{76}$ triblock copolymer.

| ABC Triblock composition | | A block | | AB diblock | | | ABC triblock | | |
|---|---|---|---|---|---|---|---|---|---|
| Targeted Morphologies | Calculation | $M_n$ | $M_w/M_n$ | Conversion of DMA | $M_n$ | $M_w/M_n$ | Conversion of DPA | $M_n$ | $M_w/M_n$ |
| Rods | PEO$_{45}$—DMA$_{29}$—DPA$_{76}$ | 3,100 | 1.08 | 96 | 8,400 | 1.18 | 99 | 19,500 | 1.20 |

The invention claimed is:

1. A method for the preparation of polymer-templated core-shell nanoparticles comprising the steps of:
   (a) preparing a cationic polymeric core material comprising polymeric micelles employing a quaternized polymer; and
   (b) coating said core material with a shell comprising silica by depositing the shell onto the polymeric micelles from at least one silica precursor at a pH of between 6.2 and 9.0 to form the core-shell nanoparticles.

2. The method as in claim 1, wherein step (a) is practiced by preparing the polymeric core material by group transfer polymerisation or controlled radical polymerisation.

3. The method of claim 1, wherein the polymeric micelles comprise copolymeric micelles.

4. The method of claim 3, wherein the copolymeric micelles comprise a diblock copolymer micelle.

5. The method of claim 4, wherein said diblock copolymer micelle has a core comprising at least one block of a first polymer and a corona comprising at least one block of a second polymer wherein said second polymer is different to said first polymer.

6. The method of claim 4 or 5, wherein said copolymer comprises a first polymer and a second polymer which both comprise amino-group comprising (alk)acrylate monomer units.

7. The method of claim 6, wherein said (alk)acrylate units comprise acrylate units.

8. The method of claim 3, wherein the copolymeric micelles are formed of a copolymer which comprises poly[2-(diisopropylamino)ethyl methacrylate)-block-2-(dimethylamino)ethyl methacrylate] (PDPA-PDMA).

9. The method of claim 8, wherein step (a) is practiced by controlling the degree of polymerisation of the PDPA-PDMA copolymer is controlled such that the mean degree of polymerisation of the at least one PDPA block falls in the range of 20-25.

10. The method of claim 9, wherein the degree of polymerisation of the PDPA-PDMA copolymer is such that the mean degree of polymerisation of the at least one PDMA block falls in the range of 65-70.

11. The method of claim 1, wherein the nanoparticles formed by step (b) have an average specific size (g) of about 300 nm or less.

12. The method of claim 1, wherein the nanoparticles formed by step (b) have an average particle size is in the region of from 10-100 nm.

13. The method of claim 1, wherein the nanoparticles formed by step (b) have an anisotropic rod-like morphology.

* * * * *